United States Patent [19]
Abrams et al.

[11] Patent Number: 5,871,517
[45] Date of Patent: Feb. 16, 1999

[54] CONVULSIVE THERAPY APPARATUS TO STIMULATE AND MONITOR THE EXTENT OF THERAPEUTIC VALUE OF THE TREATMENT

[75] Inventors: Richard Stephen Abrams, Chicago, Ill.; Conrad Melton Swartz, Johnson City, Tenn.

[73] Assignee: Somatics, Inc., Lake Bluff, Ill.

[21] Appl. No.: 784,128

[22] Filed: Jan. 15, 1997

[51] Int. Cl.$^6$ .............................. A61N 1/32; A61N 1/36

[52] U.S. Cl. .............................................. 607/45; 607/62

[58] Field of Search ........................................ 607/45, 62

[56] References Cited

U.S. PATENT DOCUMENTS

| | | | |
|---|---|---|---|
| 4,873,981 | 10/1989 | Abrams et al. | 607/45 |
| 5,269,302 | 12/1993 | Swartz et al. | 607/45 |
| 5,626,627 | 5/1997 | Krystal et al. | 607/45 |

*Primary Examiner*—William E. Kamm
*Assistant Examiner*—Carl H. Layno
*Attorney, Agent, or Firm*—Eliot S. Gerber

[57] ABSTRACT

In medical convulsive therapy (CV), comprising electroconvulsive therapy (ECT) and magnetoconvulsive therapy (MCT), a computer system is used to analyze the effectiveness of the treatment. In one embodiment the effectiveness is determined by measuring the physiological effects on the heart (ECG) muscles (EMG) and brain (EEG).

53 Claims, 8 Drawing Sheets

CONVULSIVE THERAPY APPARATUS TO STIMULATE AND MONITOR THE EXTENT OF THERAPEUTIC VALUE OF THE TREATMENT

BACKGROUND

1. Field of the Invention

The present invention relates to medical apparatus and methods for convulsive therapy (CT), namely, electroconvulsive therapy (ECT) and magnetoconvulsive therapy (MCT), and methods for automatic measurements of electroencephalographic, electrocardiographic, and/or electromyographic events that occur during treatment with CT.

2. Description of the Related Art

In ECT generally two electrodes are applied to the head of the patient, one over the right temple and the other in a second location that is commonly either by the vertex of the head or over the left temple. A small amount of electricity in a selected wave or pulse form is applied through these electrodes. The aim of the application of this electricity is to cause a generalized centrencephalic seizure, also called a grand mal seizure. Such a seizure has therapeutic value for several mental illnesses, including depression, mania and schizophrenia (Abrams, 1992). A report of a panel of the National Institute of Mental Health in *Science* (Jun. 28, 1985, pp. 1510–1511) concluded that "not a single controlled study has shown another form of treatment to be superior to ECT in the short-term management of severe depressions."

Alternatively, the generalized centrencephalic seizure (grand mal seizure) may be induced by a pulsed magnetic field from a magnetic coil positioned proximate the patient's head. This procedure, called magnetoconvulsive therapy (MCT), is described in U.S. patent application Ser. No. 08/231,307 (allowed) to Abrams and Swartz, incorporated by reference herein. The description which follows generally employs examples of electroconvulsive therapy (ECT), since it is widely used and has been extensively researched. However, the methods and systems of the present invention are equally applicable to magnetoconvulsive therapy (MCV). The term "convulsive therapy" (CV), as used herein, includes both ECT and MCT as well as chemically induced convulsive therapy.

In ECT the physician-operator determines the dose of the electrical charge for the stimulus, which is the duration of the applied current. This is determined on the basis of the patient's age, sex, concurrent medications, and response to previous sessions of ECT. The physician may, with currently available apparatus, select an electrical dose likely to provide therapeutic value. These would be in the range of 0.25 to 1.5 millisecond pulse width of fixed current within the range of 0.8 to 1.0 amperes given at a rate of 40 to 140 pulses per second over a period of 0.1 to 11 seconds. For example, selection of the "Thymatron DG" instrument (TM of Somatics, Inc., Lake Bluff, Ill.) can provide a series of brief electrical pulses of 0.9 amperes and 0.5 millisecond pulse width given at a rate of 140 pulses per second for a period that is adjustable by the physician, from 0.4 to 8.0 seconds.

CT seizures differ in their intensity, nature and therapeutic value, and it is of importance to assure effectiveness in treatment by the measurement and description of bodily phenomena that are associated with the therapeutic value. The generalized centrencephalic seizure is accompanied by a variety of measurable physiological effects in the body. These physiological effects include generation of patterns of electrical activity by the brain (electrical brain waves) which are measurable on the head with an electroencephalograph (EEG), acceleration of the heart rate which is measurable on the chest with an electrocardiograph (ECG), and contractions of skeletal muscles which are measurable with an electromyograph (EMG). Measurable effects on the EEG, ECG and EMG can occur not only during the seizure, but usually on the EEG and ECG for several minutes afterwards, and sometimes on the EEG for several weeks afterwards. The form and intensity of the physiological effects presumably reflect the nature, intensity and therapeutic value of the CT seizure. Several studies have described relationships between physiological measurements and therapeutic value of the CT seizure. In addition, several logical considerations indicate several strong expectations of such relationships, most particularly that physiological signs of greater intensity, or extent, correspond to CT seizure of greater intensity or extent, which is of greater therapeutic benefit.

Several aspects of the EEG that are of interest to the operator cannot be judged by sight impression and must be measured, but are difficult to measure with a conventional EEG paper recorder, because of large time needs, tedium, imprecision and complexity. It is not part of the training of doctors to be trained to deal with data processing, and few doctors are knowledgeable about these subjects. Accordingly, present practices by doctors do not include such measurements; rather, doctors either do not attempt to judge the therapeutic value of the CT seizure or they do so only through the occurrence of a seizure of ordinary length, or by rough impressions about the shape of the EEG, as shown on a graph made by a paper recorder (Nobler et al 1993).

The inventors' prior U.S. Pat. Nos. 4,878,498; 4,873,891 and 4,870,969 are directed to monitoring the patient in ECT and these patents are incorporated by reference herein. U.S. Pat. No. 5,269,302 discloses various systems using EEG, EMG and ECG and provides indications of the termination of seizure.

SUMMARY OF THE INVENTION

An apparatus and method is provided for the computer-automated measurement and calculation of specific characteristics of the EEG, the ECG or the EMG, or any combination of these characteristics. These measurements are made during the ECT seizure, and after the seizure. The measurements are made by a monitoring system that is electrically integrated with a device that delivers the CT stimulus. A switching device disconnects the monitoring system from its monitoring electrodes during the stimulus to protect the monitoring system. The results of the measurements and of their combinations are displayed as an alphanumeric display via lights, liquid crystal panel, paper or a cathode-ray tube. An audible or visual signal indicates the measured quality and expected therapeutic value of the treatment.

In one embodiment the signal is based on measurements only of the EEG. In another embodiment the signal is based on measurements only of the ECG. In another embodiment it is based on measurements only of the EMG. In other embodiments it is based on combinations of measures of any two or more of EEG, ECG and EMG, on two, three, four or more separate channels. In other embodiments EEG measurements are taken prior to treatment to obtain baseline measurements.

Through the automation of data collection and processing, and the automation of display, by the CT device of the resultant measured characteristics of the treatment, this invention makes such measurements practical. It decreases the time needed by the doctor to make such measurements, removing the need for sophistication by the doctor in data management and computer usage, and accordingly improves the efficiency of the doctor's services. In the present-day provision of health care services, if a new monitoring procedure requires substantial extra time or difficulty it is not generally accepted or used by psychiatrists. Accordingly, the present invention automates functions to provide decreased time by the doctor, improves ease of use and integrates all the CT application and patient monitoring functions into a single device.

The EEG aspects of interest for precise measurement include the area under the curve of the absolute value of the EEG voltage ("EEG area"), the EEG area per unit time ("EEG area rate"), and the times of occurrence of maxima and minima of the EEG area rate and coherence. The manual determination of these EEG aspects, from a paper recorder graph, would require hundreds to thousands of measurements of individual points which would have to be examined, by an expert, under high magnification.

The EEG area rate and the coherence are of interest during several time periods, including during the seizure, immediately after the seizure to 5 sec (seconds) later ("early postictal"), and from the end of the seizure to 15 to 60 sec after the seizure ("later postictal") and the entire postictal period (entire post-stimulus period). The EEG areas are calculated, by the computer system portion of the device, over intervals or epochs that vary from 0.1 to 3 sec, and are typically 1 sec; these intervals are either moving or stationary. These measurements are made for the entire domain of EEG frequencies that vary from 2 to 49 Hz (Hertz) or in any range of frequencies within this domain, or in any combination of such ranges. Measurements of the EEG voltage are taken (sampled) from 100 to 2000 times per second, and typically 1000 times per second by the A/D (analog/digital) converter. The amplitudes of EEG voltage within particular frequency ranges are obtained by a Fast-Fourier Transform ("FFT") calculation program that is a part of the device.

Among several methods to measure the EEG amplitude, the EEG area rate is preferred. That area rate is obtained by numerically integrating the values for the samples to obtain the total area under the curve connecting these values, and then dividing by the amount of time over which the samples were taken; all areas are counted as positive. For example, if the interval is selected to be 0.1 seconds, and the sampling rate is 1000 per sec., then a curve is fit to the 100 samples and the total area between the curve and the x-axis is calculated by the ordinary mathematical procedures of numerical integration. This area is then divided by 0.1 seconds to obtain the area rate. The EEG area rate has the virtue of incorporating all EEG seizure activity and of including negative voltages, the physiologic meaning of which does not differ from positive voltages. Use of the EEG area rate also allows the attribution of EEG area rates to separate frequency bands, for example, using FFT calculations. Numerical integration methods with curve fitting should generally be more reflective of total EEG activity than simple averaging.

Other measures of EEG amplitude are the maximum positive EEG amplitude and the maximum absolute EEG amplitude within defined time epochs, such as 0.5 sec. These describe maximums while the EEG area rate describes a sequence in time.

The measured aspects of the EEG are stored and used in combination to form additional characterizations of the seizure. These additional characterizations include the maximum ictal EEG area rate and the minimum postictal EEG area rate, both taken over 1-second periods. The maximum EEG area rate represents the peak intensity of the seizure, and the minimum EEG area rate represents the peak suppression of EEG activity produced by the seizure, which is an indirect summation of the anticonvulsant effects of the seizure.

Preferably these measures are compared with each other and with measured pre-treatment baseline values, and these measures are used in combination. The baseline values may be obtained from the patient prior to treatment (self-norm) or may be based on norms (statistical data) gathered from a control group (group norm) similar in age and gender to the patient.

In addition, to minimize the influence and likelihood of artifacts, particular limits can be placed on the baseline values according to experimental measurements of population ranges. Of particular interest is the ratio of the minimum EEG area rate divided by the maximum EEG area rate; the difference between that ratio and unity represents the maximum fraction (or percentage) of suppression of seizure activity. Another ratio of particular interest is the minimum EEG area rate divided by the pre-treatment baseline EEG area rate; this represents the suppression of baseline EEG activity consequent to the seizure.

Likewise, several aspects of the electrocardiogram (ECG) are of interest to operators but are tedious, imprecise or impractical to judge by sight or by manual measurement obtained from a paper recorder. There is typically an abrupt onset of an elevation in heart rate at the beginning of the seizure, and an abrupt heart rate decrease shortly after the end of the seizure. The aspects of particular interest on the ECG are the peak heart rate and the duration of heart rate elevation within defined limits, such as within 10% of the peak heart rate (at that treatment), within 10% of a pre-set rate, or above 125% of the heart rate just prior to the stimulus. Such measurements enable further comparisons of interest to the operator of the instrument, such as the comparison of the peak heart rate of the present treatment with the patient's peak heart rate in previous treatments.

Likewise, several aspects of the electromyogram (EMG) are of interest to operators but are tedious, imprecise or impractical to judge by sight or by manual measurements from a paper recording. These include measurements of the number and rate of muscle-generated electrical spikes during the seizure. Measurement of EMG and ECG voltage are preferably sampled from 30 to 2000 times per second, and typically 200 times per second for ECG, and typically 300 times per second for EMG.

The present invention provides a single apparatus which delivers the CT stimulus and monitors the patient, e.g., measures the patient's response to the treatment. The instrument uses a single computer system, preferably with a single master microprocessor, to control both its ECT electrical stimulus or MCT magnetic stimulus and monitoring functions. The apparatus delivers an CT stimulus to the patient and uses a method in CT, employing digital computer-based algorithms, to determine and display characteristics of one or more of the EEG, ECG and EMG voltages that follow the delivery of the CT stimulus. These characteristics describe CT seizure occurrence, endpoint, length, and several aspects of seizure quality, including intensity, extent, coherence, generalization and spread through the brain, and consequent postictal suppression of these same activities as a further description of their effect.

It is an objective of the present invention to provide determinations of the quality of the therapeutic effect of the treatment without the necessity for manual measurements, special medical expertise, expertise in electrical signal processing, expertise in digital data handling or computer processing, or familiarity with EEG, EMG or ECG patterns of CT seizures. This serves to decrease the physician's time and training required for judgments about the therapeutic value of the treatment.

It is a further objective of the present invention to provide such an apparatus and method to allow uniformly standardized descriptions of the measured characteristics of the CT seizure, which descriptions are applicable to all patients regardless of their medical condition.

It is a further objective of the present invention that the measurement procedures be non-invasive.

It is a further objective of the present invention to process the data from the EEG, on the operator's choice, of either one channel or two channels.

It is a further objective of the present invention to simultaneously process three, four or more channels of physiological data from the CT, such as two channels of EEG and one channel of ECG, or two channels of EEG and one channel of EMG, or one channel each of EEG, ECG and EMG, or two channels of EEG with one channel of EMG and one channel of ECG.

BRIEF DESCRIPTION OF THE DRAWINGS

Other objectives of the represent invention will be apparent from the following detailed description, taken in conjunction with the accompanying drawings.

In the drawings.

DETAILED DESCRIPTION OF THE INVENTION

The apparatus and method of the present invention automatically, continuously and repeatedly measures one or more particular aspects of the ECG, EMG, EEG, alone or in combination, and compares these measurements to the patient's pre-CT level to determine the occurrence, duration, termination, generalization, intensity, coherence, character and quality of the induced therapeutic seizure of convulsive therapy.

This description uses the electroconvulsive therapy (ECT) in its examples; however, its monitoring of seizure is also applicable to other types of CV, especially magnetoconvulsive therapy (MCT).

Figure 1:
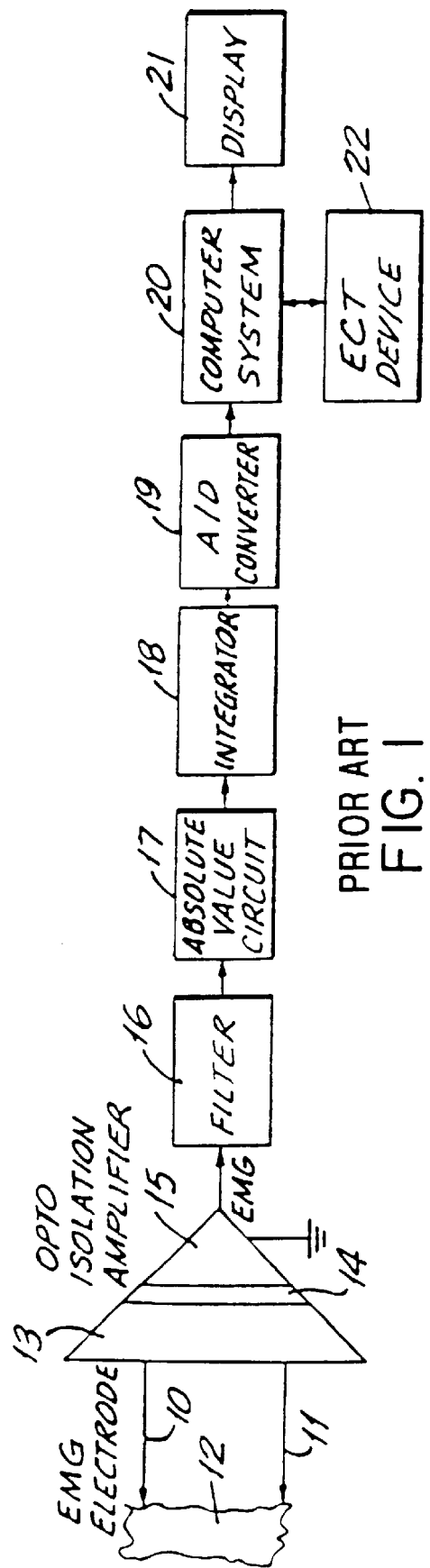
FIG. 1 is a block diagram of the first embodiment of the present invention.

In the first embodiment shown in FIG. 1, the EMG is sensed via three disposable or reusable electrodes, including 10 and 11 pasted on a limb 12 of the patient. The patient's limb is injected with a muscle relaxant drug. The patient's arteries have previously been occluded, by external pressure from a tourniquet or sphygmomanometer (air expandable cuff), in order to limit the muscle relaxant drug, and its effects, to the distal musculature (the muscles of the limb). The electrodes 10 and 11 are pasted over a major muscle group.

The electrical signals produced by the muscles of the patient's limb and detected by electrodes 11 and 12 are amplified with a differential amplifier 13. For patient safety the EMG signals are isolated with an optoelectronic isolator 14. The EMG signals are then further amplified by amplifier 15 and the signals' frequencies are limited with a 2–100 Hz filter 16. The amplified signals are then passed through an absolute value circuit 17 and an integrator 18 to provide the mean value of the EMG. The mean analog value is then sampled and digitized by the analog-signal (A/D) converter 19 at the millisecond rate (1000–10,000 samples/sec./channel) to provide digital data. The computer system 20, connected to A/D converter 19, calculates the time of the steepest drop in the EMG voltage. The baseline (pre-stimulus) computed EMG voltage may then be calculated and generated by the computer system 20, e.g., as the average wide-band integrated voltage taken over 5 seconds. Alternatively a reference level (baseline) based on data obtained from other patients ("norms") may be used to determine the baseline (reference). The computer system 20 preferably includes a single chip 8 or 16 or 32 bit microcomputer (microprocessor), for example, a 16-bit HD68000 available from Hitachi (a NMOS chip available in a DC-64 package) or a 133 MHz "Pentium" (TM—Intel Corp).

When the collection of the baseline voltage measurement has been accomplished, the operator is signaled via an electronic display 21. He may then deliver the ECT electrical signals by triggering a switch on the ECT device 22.

Figure 4:
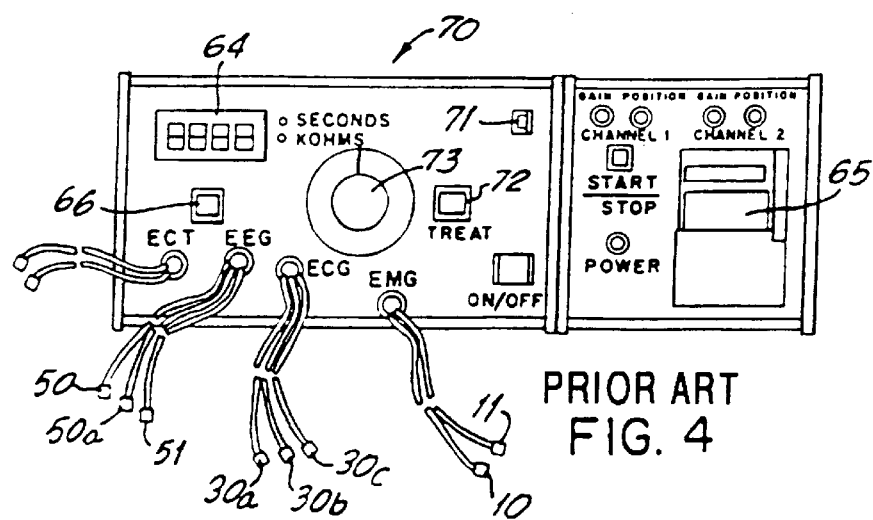
FIG. 4 is a front plan view of the device embodiment of FIG. 3.
Figure 5:
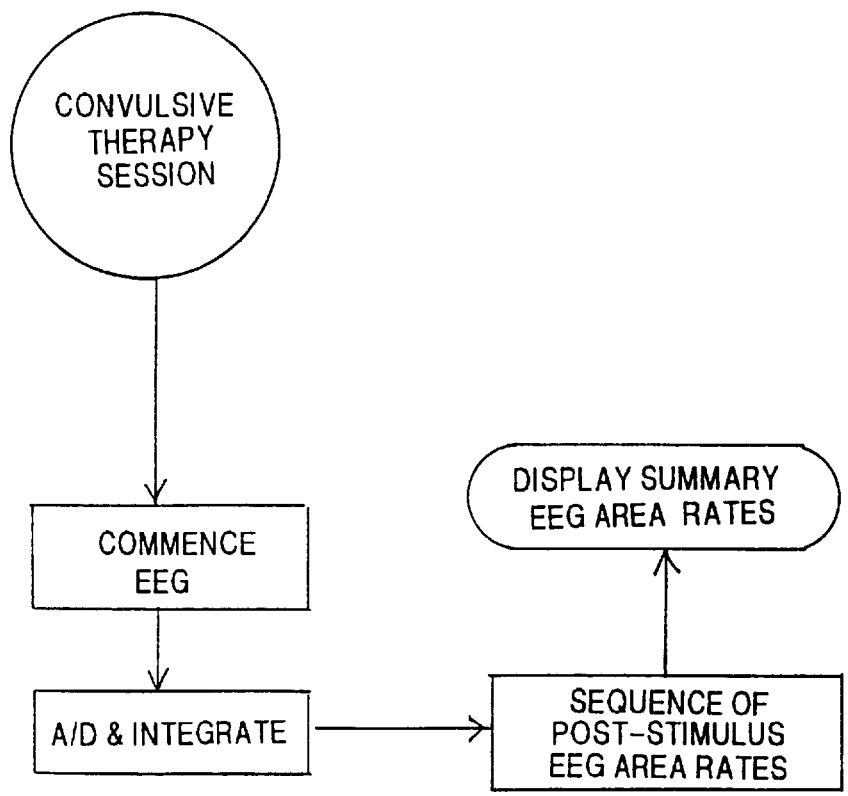
FIG. 5 is a block flow diagram illustrating the method of obtaining and displaying a sequence of EEG area rates.
Figure 6:
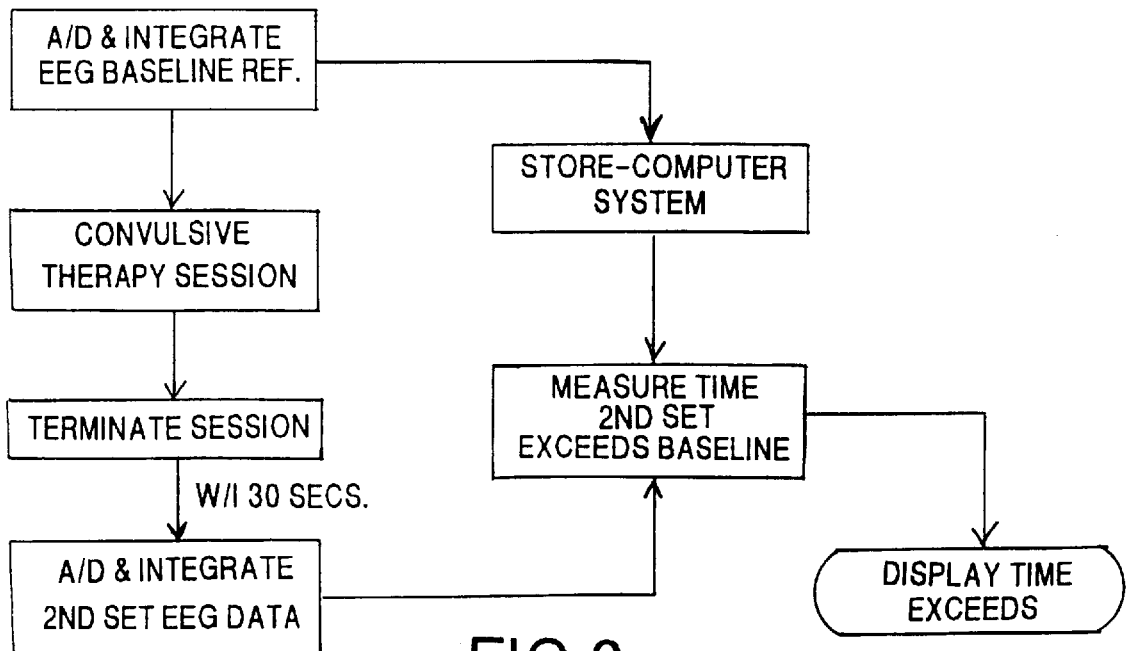
FIG. 6 is a block flow diagram illustrating the method of comparing a patient's EEG data immediately following a CT stimulus compared to a baseline EEG reference.
Figure 7:
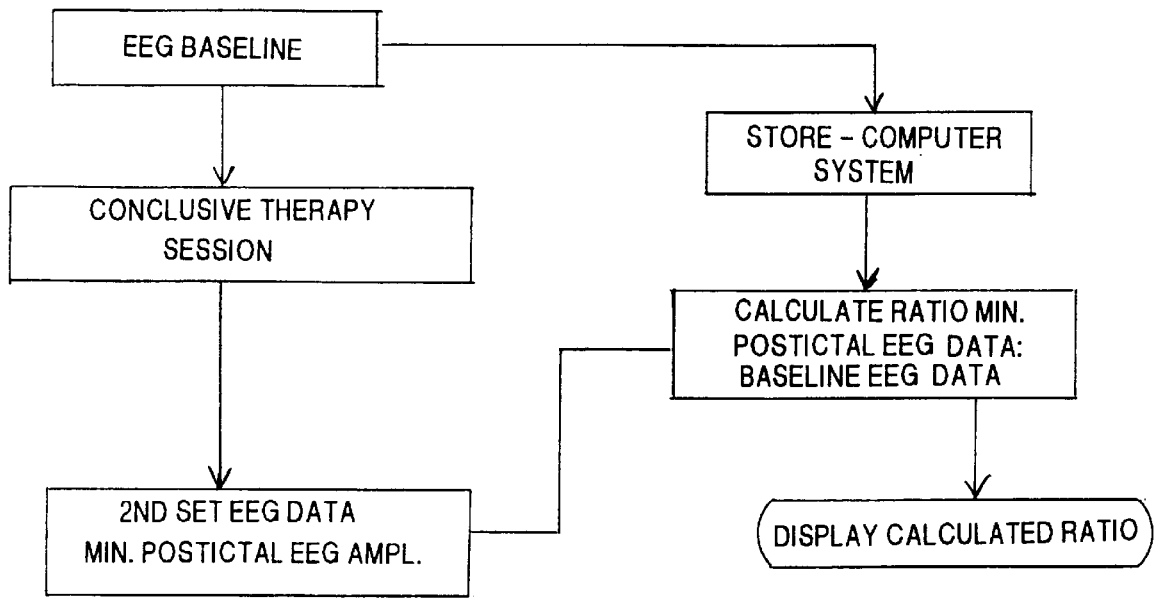
FIG. 7 is a block flow diagram illustrating the method of comparing minimum postictal EEG amplitude to baseline EEG data.
Figure 8:
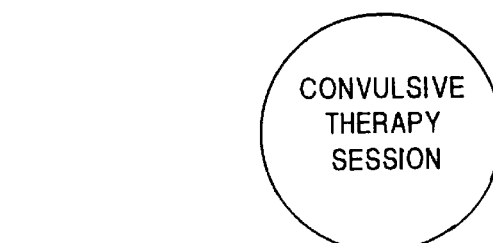
FIG. 8 is a block flow diagram illustrating the method of analyzing EEG voltage differences between samples within each pair of electrodes and displaying a seizure coherence measurement.
Figure 8:
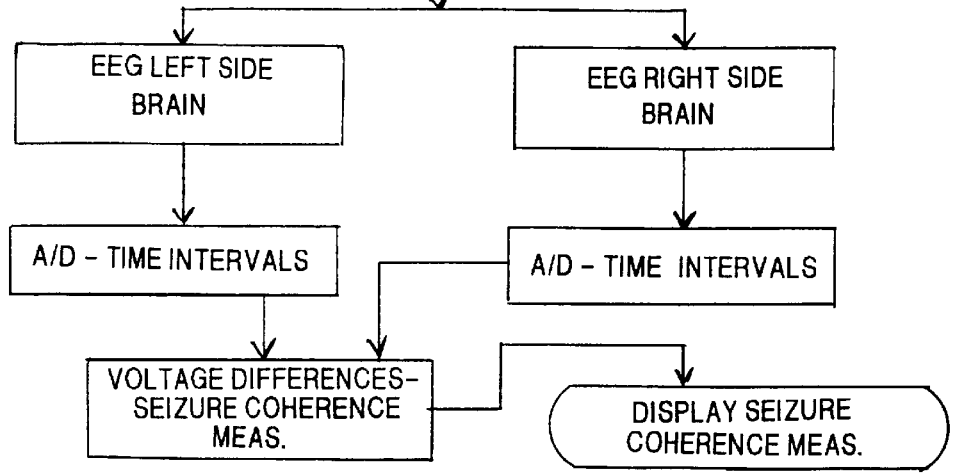
Figure 9:
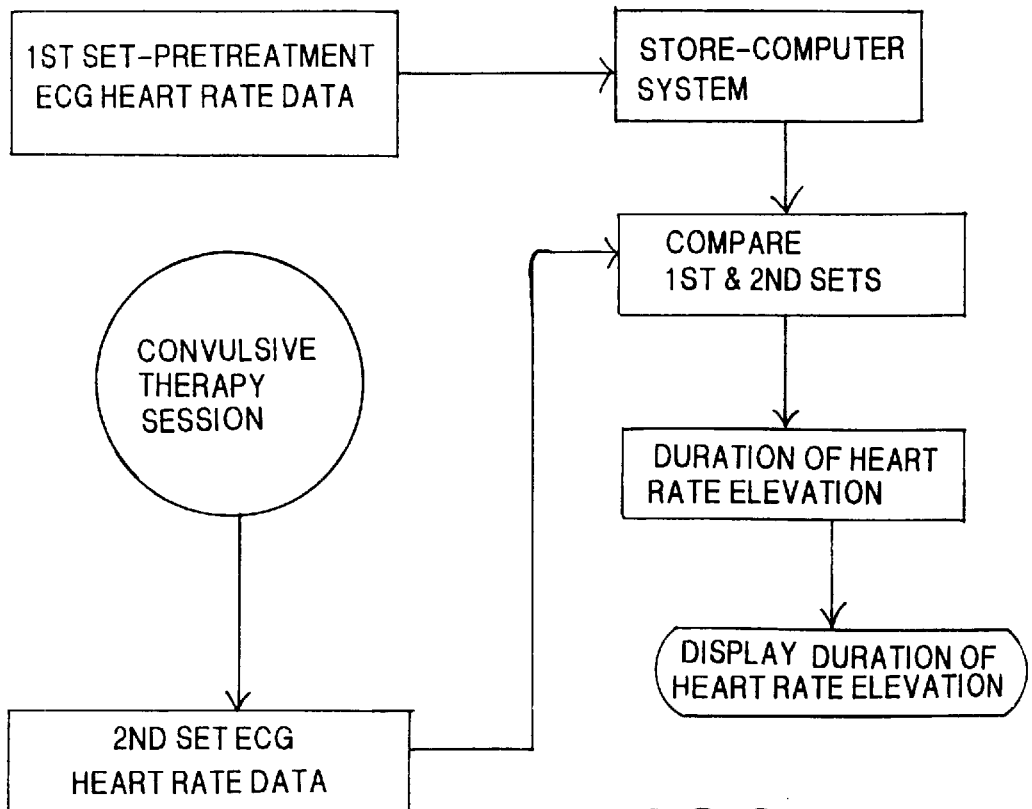
FIG. 9 is a block flow diagram illustrating a comparison involving patient heart rate data following termination of CT power.
Figure 10:
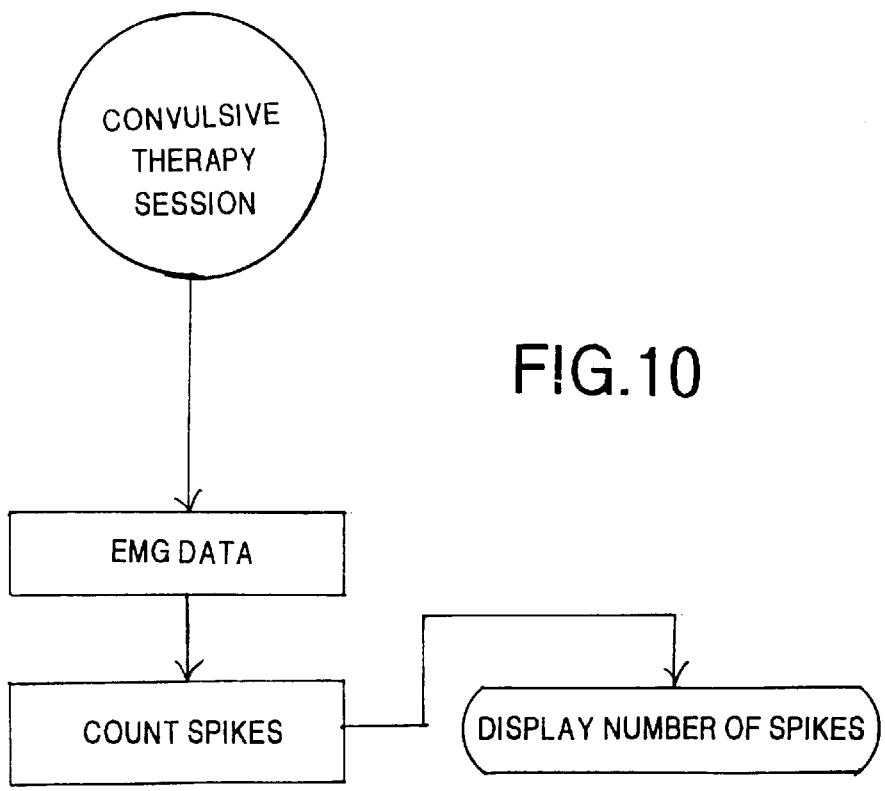
FIG. 10 is a block flow diagram illustrating a method of obtaining and displaying muscle electrical spikes following termination of CT stimulus.
Figure 11:
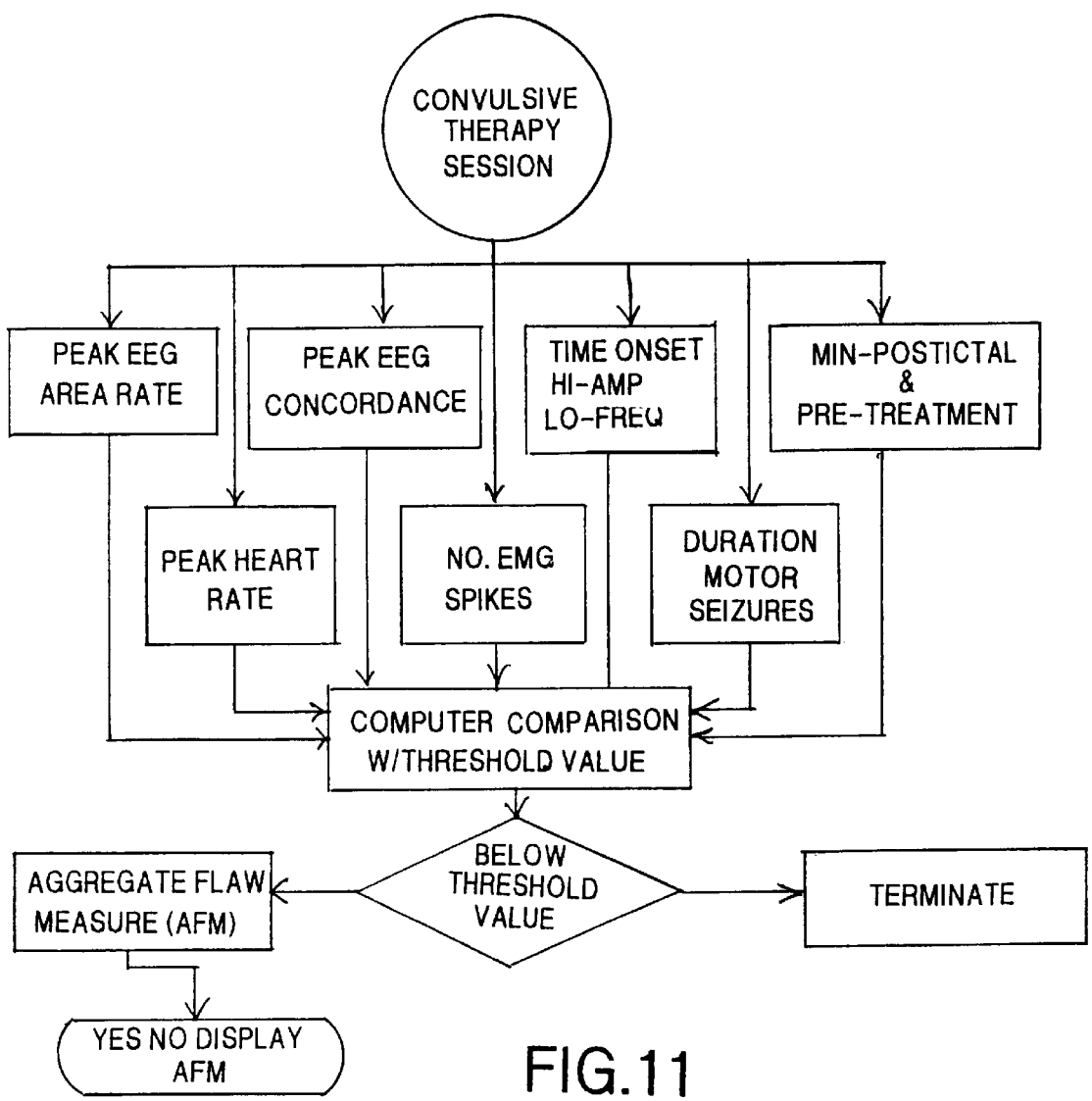
FIG. 11 is a block flow diagram illustrating a method of determining the value of at least five measures following CT therapy.
Figure 12:
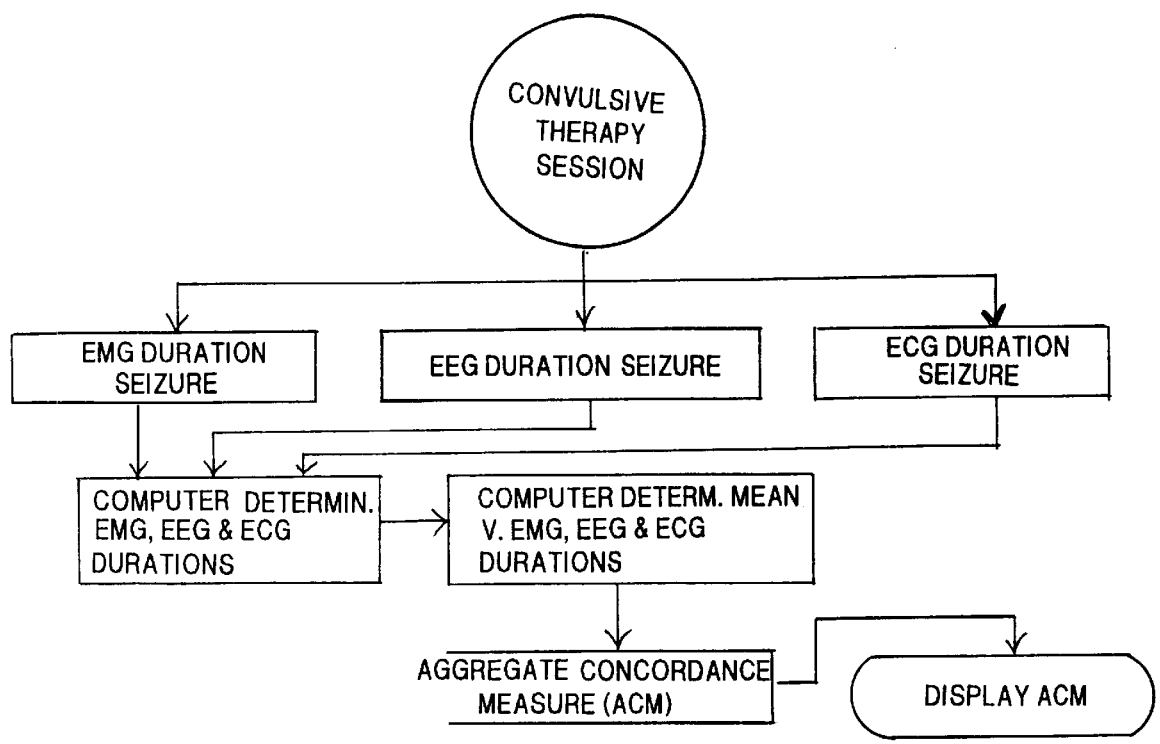
FIG. 12 is a block flow diagram illustrating obtaining and displaying an Aggregate Concordance Measure based on the duration of a CT seizure as obtained from EEG, ECG and EMG.
Figure 13:
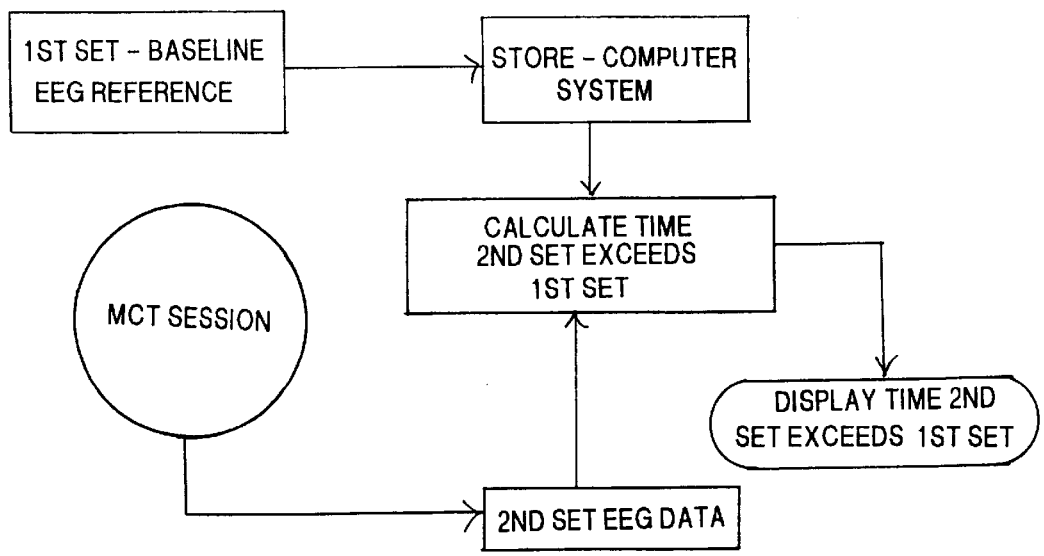
FIG. 13 is a block flow diagram illustrating a method in magnetoconvulsive therapy (MCT) which compares a patient's EEG data to baseline EEG reference data.
Figure 14:
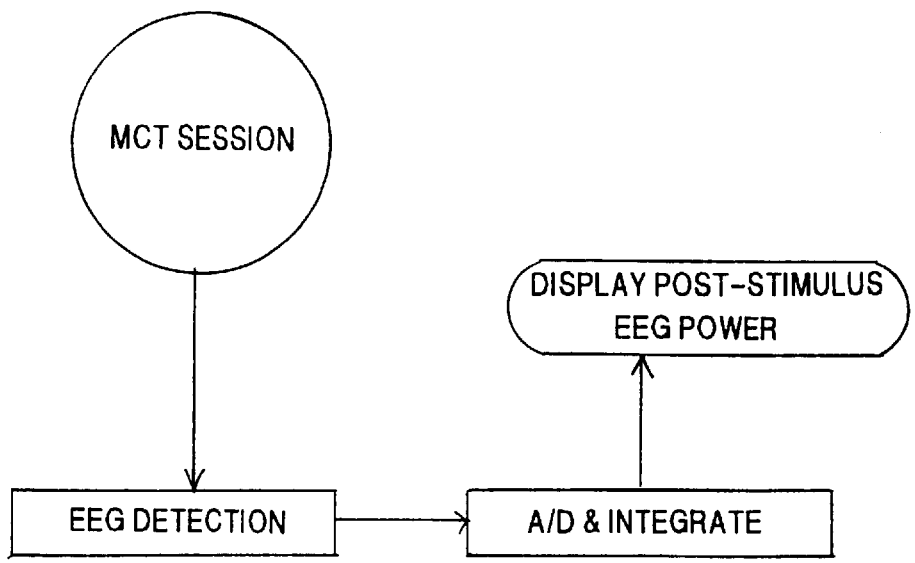
FIG. 14 is a block flow diagram illustrating a method in MCT to obtain and display post-stimulus EEG power.
Figure 15:
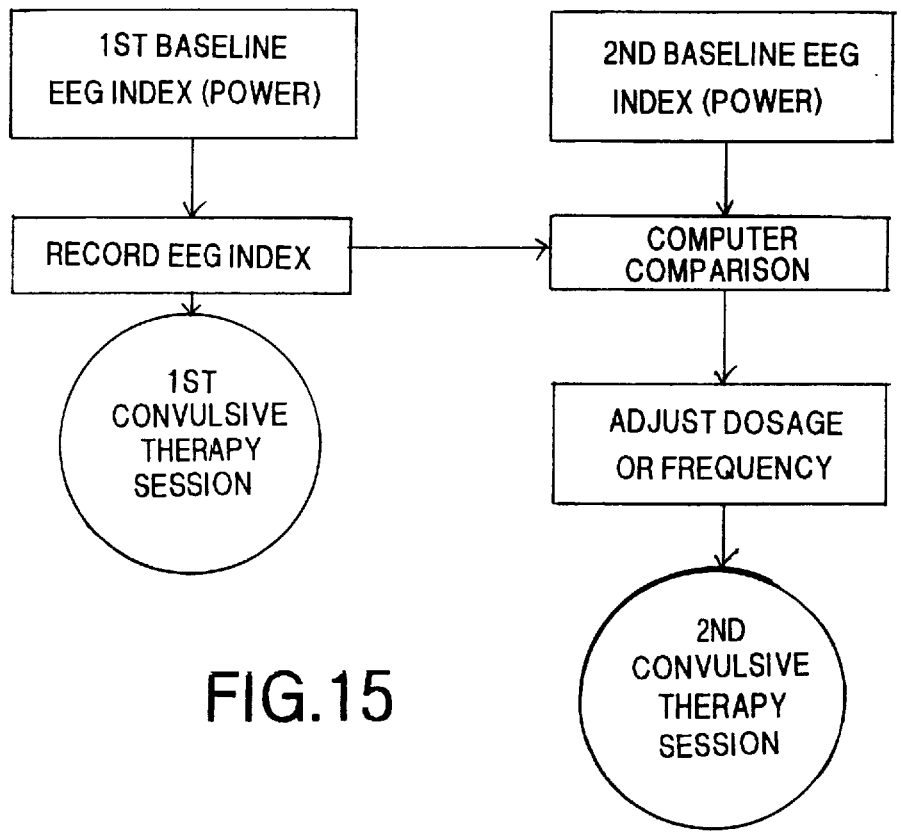
FIG. 15 is a block flow diagram illustrating a method in convulsive therapy (CV) to obtain and utilize a baseline EEG Index, which is a measure of energy or power in one or more bandwidths.

The apparatus 1 includes, in a single casing (cabinet) the circuitry to amplify the EMG, EEG, and ECG signals, filter and convert those signals, the computer system 20, the ECT device 22 and the display 21 (see FIG. 4).

Periodic repeated sampling (e.g., at least once per second, but typically 20 to 50 times per second) of the post-stimulus electronically-processed EMG voltage is automatically begun when the ECT electrical stimulus has concluded or the halt of the ECT stimulus, via 20, starts the EMG sampling. The electronically processed EMG voltage of each post-stimulus sample is compared to the pre-stimulus mean value or other selected reference value.

ECG signals are electrical potential traces of waves that accompany the contraction of the different cavities of the heart. They are an important aid in the examination of heart activity. A typical ECG signal, produced by placing electrodes against the patient's skin, includes P, Q, R, S and T waves, which are all discernable by electrodes removably connected to the patient's chest. ECG signals are commonly displayed as a wavy line made by a pen on paper. The ECG signals are taken at frequencies of 0–50 Hz, this frequency range being normally sufficient for discerning such waves since the heartbeat rate is approximately 1 per second, and the rise time of these waves is in the order of 0.1 second.

A typical heart beat consists of an initial flat isoelectric portion: a positive and rounded "P" wave, a negative "Q" wave; an "R" wave whose leading-upward slope corresponds to depolarization and whose lagging-downward slope corresponds to repolarization; a negative "S" wave; the "S-T" segment between the S and T waves; the "T" wave, and sometimes a final small "U" wave. Preferably the heart rate is determined by the time interval between R wave peaks, although alternatively other portions of the heart waves may be detected and used to determine the rate. Preferably the heart beat is detected by at least 3 electrodes, although a conventional 12-electrode system may be used.

Figure 2:
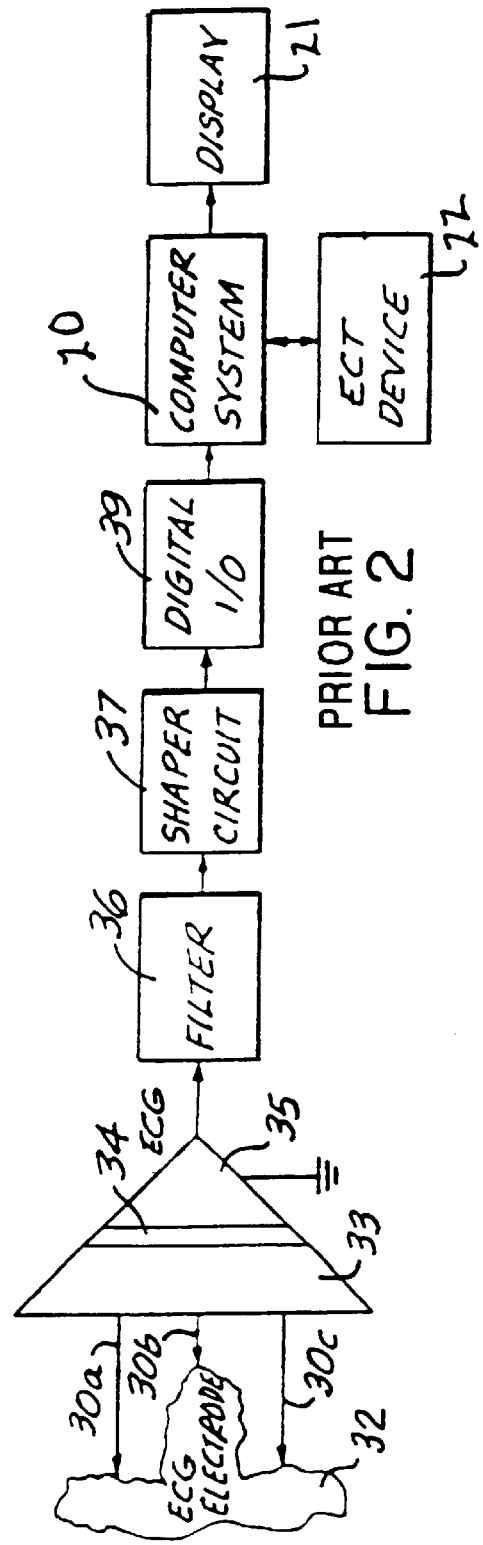
FIG. 2 is a block diagram of the second embodiment of the present invention.

In the second embodiment, shown in FIG. 2, the ECG signal (electrocardiograph), which detects heart activity, is sensed via three disposable, or reusable, electrodes 30$a$, 30$b$ and 30$c$ pasted on the chest 32 of the patient. The ECG signal is amplified with a low-noise differential amplifier 33 (less than one microvolt of noise) having a band width of 0–300 Hz. For patient safety the signal is isolated with optoelectronic isolator 34. The ECG signal is then further amplified by amplifier 35 and its frequency is then limited with a 2–50 Hz filter 36. The signal is then passed through a shaper circuit 37 which detects the R-wave of the ECG and provides a square wave output which is detected by digital in/out circuit 39 which is connected to the computer system 20. The same computer 20 is used for the measurement and analysis of EMG, ECG and EEG and it also controls the operation of the ECT.

The pulse output of shaper circuit 37 is connected to a digital input-output circuit 39 which provides a digital interrupt signal with every heartbeat, i.e., it is a rate detector. The heart rate is determined beat-to-beat by timing the interval between successive R-waves. The computer system 20 calculates the time of the steepest drop in the heart rate. The pre-stimulus (baseline) frequency is determined over a 5-second period. After the operator delivers the ECT electrical stimulus, by triggering a treatment switch on the ECT device 41, the heart rate is monitored by the apparatus 1. The heart rate usually accelerates, plateaus, and then decelerates, first abruptly and then slowly.

Figure 3:
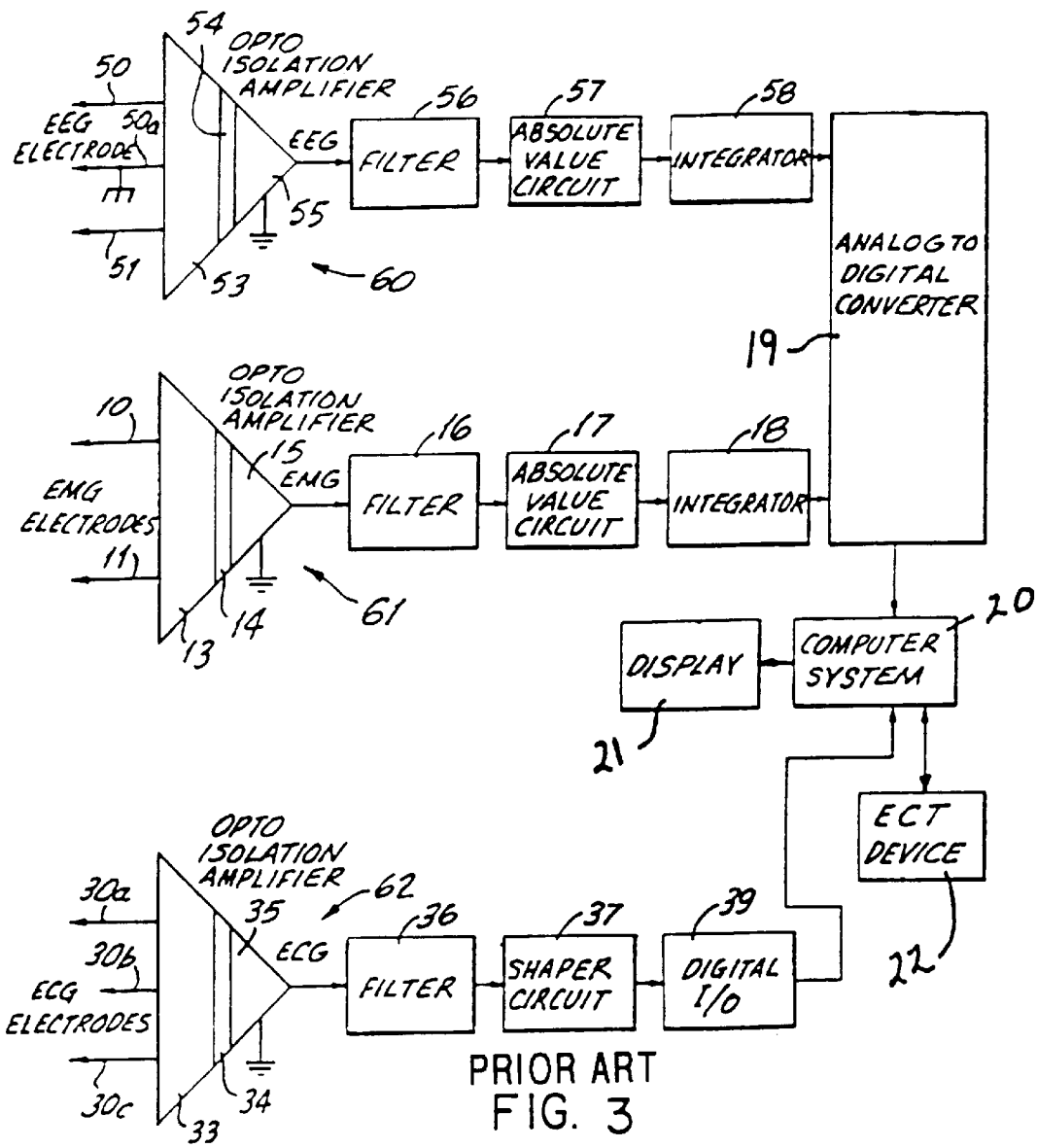
FIG. 3 is a block diagram of the third embodiment of the present invention.

In the third embodiment, shown in FIG. 3, the EEG signal (brain waves at the microvolt level) is detected at three disposable, or reuseable, scalp electrodes 50 and 51 pasted over sites on the head 52, e.g., on the forehead, typically above the eyes, or over the mastoid processes, or above one eye and over one mastoid process. The EEG signal can alternatively be sensed directly from the treatment electrodes of the ECT device if those electrodes are placed over the temple or on the forehead.

The EEG signal is amplified with a differential amplifier 53. For patient safety, the signal is isolated, to minimize unintended current exposure, with optoelectronic isolator 54. The EEG signal is then further amplified by amplifier 55 and its frequency is limited with a 2–25 Hz filter 56. The "higher brain wave frequencies" are in the range 12.5–25 Hz and the "lower frequency" brain waves are in the range 2–7.5 Hz. The signal is then passed through an absolute value circuit 57 and an integrator 58 to provide the mean value of the EEG. The mean analog value is then sampled and digitized by an analog-to-signal (A/D) converter 59.

The patient's brain waves, as detected by the EEG electrodes 50, 50$a$, 51 and amplified and digitized by the EEG system, shown in FIG. 3, may be used to provide additional information to the operator. The patient's brain waves are preferably detected and analyzed by computer system 20 before the treatment ("pre-treatment") to establish a baseline (reference). The treatment (stimulus) is then applied with the expectation of inducing seizure. The EEG is used post-stimulus (during the seizure) and "postictal" (after the seizure).

The EEG signal is preferably divided, by filters, into selected frequency bands within the 2–25 Hz band of filter 56. The Delta band is 2–3.5 Hz and according to published studies, constitutes most of the brain wave energy generated during the ECT-induced seizure and is considered to be the seizure's primary therapeutic component. The Theta band is 3.5–7.5 Hz, the Alpha band is 7.5–12.5 Hz and the lower portion of the Beta band is 12.5–25 Hz. Preferably the "absolute power" in the Delta band (2–3.5 Hz) is measured, although alternatively or in addition absolute power across the entire 2–25 Hz spectrum may be measured or absolute power in other bands may be measured. The "absolute power" is the mean integrated voltage in the selected band taken over the duration of the ECT-induced seizure.

This third embodiment provides three independent channels of digital data, channel 60 for EEG, channel 61 for EMG, and channel 62 for ECG. Each channel 60–62 is connected to the computer system 20 and presents digital data to the computer system 20, as in the prior embodiments. The computer system 20 controls ECT device 22 and performs analysis on each channel (i.e., on the EEG, ECG and EMG) and then combines their comparisons of the first and second sets of digital data to present a unified determination which is displayed on the display 21.

In the embodiments using EEG two pairs of electrodes may be placed over mirror-image sites on both left and right sides of the head, e.g., above both eyes, over both mastoid processes, or from two treatment electrodes placed bifrontally or bifrontotemporally. The coherence of the EEG signal, which is a comparison of EEG signals on the right and left sides of the head, is measured, ongoing, beginning 5 seconds after the end of the ECT stimulus. An abrupt reduction in coherence signals the end of the seizure. The time-integrated amplitude of coherence until the end of the seizure reflects the quality of the seizure.

The Seizure Coherence measurements are obtained by removably connecting half the electrodes on the left side of the head, and the other electrodes are distributed on the right side of the head. Their locations are the mirror images of the electrode locations on the left side of the head. The less the voltage difference between mirror image electrodes (within each pair) the greater the coherence. In one embodiment, voltage differences from pairs of mirror image electrodes are subtracted from a mean voltage, and the time sequence of sums of absolute values of these voltage differences is taken and displayed as the Seizure Coherence. In another embodiment, differences between electrodes over the left side of the head are subtracted from differences between mirror image electrodes over the right side of the head; this resultant difference is then subtracted from a mean voltage, and the time sequence of the absolute values of these voltage differences is taken and displayed as the Seizure Coherence. In another embodiment, the correlation is calculated between the voltage time course from an electrode and the voltage time course from its mirror image electrode, over a moving time interval such as one second and the regression coefficient or correlation coefficient is calculated and displayed as the Seizure Coherence.

Coherence measurements are made during the seizure as momentary peak coherence or as maximum peak coherence over a specific duration such as 10 sec. Coherence measurements would additionally be made after the seizure, as the momentary minimum coherence or the minimum nadir coherence over a specific duration such as 10 sec. Coherence measurements would also be made before the stimulus to form a baseline for comparison. Coherence measurements can be restricted to a specific range of EEG frequencies, such as 5.5 to 12 Hz, or 2.5 to 5 Hz, or 13 to 30 Hz, or they might cover all frequencies from 2 to 30 Hz.

As shown in FIG. 3, the device 70 includes four conductive EEG electrodes 50, 50a and 51, two conductive EMG electrodes 10 and 22, and three conductive ECG electrodes 30a, 30b and 30c, all of which are removably applied to the skin of the patient. The minimum number of electrodes required for each of the EEG, EMG or ECG is two plus one ground electrode for the system, i.e., seven electrodes; and determination of EEG coherence requires two additional electrodes, for a total of nine.

As shown in FIG. 4, the electrode impedance is tested by the test button 66 and the impedances shown on display 64. The baseline (reference) of the EEG, EMG and ECG may be obtained by pushing the baseline button 71. Preferably the baseline (first set of digital data) for the EEG, EMG and ECG is obtained by measuring the patient twice prior to ECT, and averaging the data from both tests. The ECT treatment is started by pushing "treat" button 72 and the time for the treatment is selected by adjustable timer 73. The various measurements are shown on display 64 and are also preferably printed out by printer 65.

Concerning observations of the EEG, larger electrode stimuli were associated with higher EEG amplitude and greater coherence during the seizure, particularly in the ranges of 2–5 Hz and 5–5.13 Hz, and lower EEG amplitude in the range from 2 to 5 Hz following the seizure (Krystal et al. 1993). Because larger stimuli tend to be more effective, there is the implication that greater treatment effectiveness will be accompanied by higher amplitude and coherence during the seizure, and greater postictal suppression.

Right-unilateral ECT given with a low electrical dosage was less clinically effective than right unilateral ECT given with a higher electrical dosage. The right-unilateral ECT of lower effectiveness was accompanied by less postictal suppression on the EEG and lower EEG seizure amplitude in the range of 2–5 Hz (Nobler et al. 1993). This provides further evidence that greater postictal suppression and higher EEG seizure amplitude reflect greater effectiveness of the ECT treatment.

Larger electrical stimuli in the same patients receiving right-unilateral ECT produced EEGs with greater seizure amplitude, seizure coherence, and postictal suppression, and shorter latency to the onset of high-amplitude low-frequency waves during the seizure (Krystal et al 1995). More rapid response was associated with greater postictal suppression in the range of 5–30 Hz and lower postictal coherence in the 2–5 Hz range, in a group of patients who received right-unilateral and bilateral ECT (Krystal et al 1996).

When bilateral ECT is administered with a stimulus dose low enough that no motor seizure activity occurs and the only evidence of seizure is on the EEG, the EEG shows only low-frequency waves and little high-frequency activity, and the clinical effectiveness is unusually low (Christensen et al 1986). Likewise, when lidocaine is given to patients before ECT to diminish the intensity of the seizure, the EEG shows virtually only low-frequency waves and little high-frequency activity during the seizure.

Taken together, these observations indicate that greater clinical effectiveness is generally reflected by higher EEG area rate, higher coherence, and shorter time to the onset of high-amplitude low-frequency waves during the seizure, and also postictally by a lower EEG area rate and less coherence. The "EEG area rate" is the integral over time of the curve that connects the digital samples taken over a selected time, divided by the amount of time over which the samples were taken, in which all area is counted as positive. For example, if the A/D conversion sampling rate is at 1000 samples per second and the selected period is 0.1 seconds, then the EEG area rate is the absolute value of the area under the curve that is fit to the 100 sample points taken over the 0.1 seconds time period, this area then divided by 0.1 seconds. The EEG area rate may be taken over one second; but because an ECT seizure should last at least 18 seconds (Swartz & Laran 1989), the sustained EEG area rate should be considered over at least several seconds, for example, for 10 seconds. A corresponding measure is the largest average EEG area rate over a continuous 10 second period. Another corresponding measure is the largest coherence over a continuous 10 second period; the period of peak coherence might, or might not, coincide with the period of the largest EEG area rate.

The observations further indicate that preferably these measurements are based on a limited range of EEG frequencies. The absence of high-frequency activity on the EEG is a sign of low clinical value of the ECT treatment, a principle also suggested by comparisons of different measures of seizure duration (Swartz 1995). The EEG area rates in various ranges of EEG frequency are found by the application of computer program and using the Fourier Transformation, and specifically the Fast Fourier Transformation (FFT). This method has the additional virtue of allowing the identification of artifactual electrical signals on the EEG and the subsequent removal of these signals and their influences. Such artifactual signals are frequently present and arise from, for example, movement of the cables that connect the recording electrodes an the ECT instrument, as commonly occurs when the anesthetist unwittingly touches these cables while ventilating the patient. The automatic identification and removal of such artifactual signals from the data set may be impractical without the use of the FFT.

It is desirable to consider not only the particular values of the EEG area rate, amplitude and coherence, but also to consider comparisons such as ratios of these characteristics from one time to another, in view of large variations of these characteristics among patients. The comparisons are automatically performed by the internal computer system of the device, which has been software programmed. Preferably, the comparisons are expressed as ratios. Specifically, the ratio of the EEG area rates at peak are compared to a before-treatment baseline. That ratio describes the amount of increase in brain electrical activity from the seizure. The ratio of the EEG area rates, at the minimum, after the seizure are compared to a before-treatment baseline to describe the amount of suppression of resting brain electrical activity consequent to the seizure. It has the virtue of not depending on the determination of the seizure endpoint and the errors associated with that determination. The ratio of the EEG area rate at the minimum after the seizure is compared to the EEG area rate peak during the seizure to represent the amount of suppression of brain seizure activity. Ratios among the EEG coherences before treatment, at the maximum during the seizure, and at the minimum after the seizure have similar meanings. A table of these ratios is set forth in Table I below.

TABLE I

| 1. | EEG area rates at peak (after seizure): EEG area rates baseline (before stimulus) |
|---|---|
| 2. | EEG area rates, minimum (after seizure): EEG area rates baseline (before stimulus) |
| 3. | EEG area rates, minimum (after seizure): EEG area rates at peak (during seizure) |
| 4. | EEG coherences (during the seizure): EEG coherences baseline (before stimulus) |
| 5. | EEG coherences, maximum (during the seizure): EEG coherences baseline (before stimulus) |
| 6. | EEG coherences, minimum (after the seizure): EEG coherences baseline (before stimulus) |

Concerning observations of the electrocardiogram, greater ECT effectiveness was seen in patients who showed greater increases in the product of heart rate and blood pressure (Webb et al 1990). Because carbon dioxide is an anticonvulsant and can obstruct the ECT seizure and its treatment value, hyperventilation-induced hypocapnia (i.e., diminishment of carbon dioxide levels) provides an increase in the clinical value of ECT (Swartz 1993). Accordingly, the observation that such hypocapnia is accompanied by a higher peak heart rate adds to the evidence that higher peak heart rate signals greater ECT treatment effectiveness. Consistent with this, our own studies have found that each high dose of right-unilateral ECT produced the same peak heart rate as a high-dose of bilateral ECT. (Lane et al. 1989) and also had the same clinical effectiveness (Abrams et al. 1991). In current studies, we have additionally observed that higher peak heart rate follows ECT stimuli of greater charge and longer duration, which are expected to be more effective, so that higher peak heart rate is generally a sign of greater effectiveness (Swartz and Manly, report in progress).

Accordingly, these observations indicate that greater clinical effectiveness is generally reflected by higher peak heart rate during the seizure. In particular, for high effectiveness of the ECT, the peak heart rate is generally not lower than seen in previous ECT treatments of that patient. The observations also suggest that greater clinical effectiveness is associated with longer persistence of heart rate near the peak. Such longer persistence is measured by (i) the duration of the heart rate that is within a selected percentage of the peak heart rate, for example, within 10% of the peak heart rate; and (ii) the duration of the heart rate substantially over the patient's pre-treatment resting heart rate, for example, selected to be 25% over such pre-treatment resting heart rate. Both of these measures (i) and (ii) are calculated by the internal computer system of the device, and both measures (i) and (ii) must be met to indicate clinical effectiveness of the ECT.

Concerning muscle activity during ECT seizure, observable on the electromyogram (EMG), when lidocaine is given to patients before ECT to diminish the intensity of the seizure, the tonic phase of motor seizure does not occur, and only the clonic phase is seen. When bilateral ECT is administered with a stimulus dose low enough that no motor seizure activity occurs and the only evidence of seizure is on the EEG, the clinical effectiveness is unusually low (Christensen et al. 1986). These observations indicate the presence of a relationship between treatment effectiveness and the appearance, and presumably the duration, of the tonic phase (tonus) of motoric seizure activity. The tonic phase is composed of a series of muscular contractions so closely spaced that the muscles appear to be continuously contracted; accordingly, the relationship between effectiveness and the duration of tonus is also a relationship between effectiveness and the number of electrical contractions, counted as the number of electrical spikes on an electromyograph (EMG).

Preferably all the signs of greater therapeutic benefit (or intense seizure activity) are combined to form an aggregate measure of therapeutic effectiveness. Just as high therapeutic value is associated with the occurrence of the individual signs (noted above) such as long duration of tonus in the motor seizure, high peak heart rate, and strong postictal suppression on the EEG, low therapeutic impact is associated with the non-occurrence of these signs. In analogy to the strength of a chain being that of its weakest link, the therapeutic strength of the treatment is in doubt when there is non-occurrence of an individual sign of sufficient treatment. The consideration of several or all these signs together comprises aggregate measures of the treatment value. These aggregate measures reflect the observation of seizure activity in several different regions of the brain, and accordingly represent the generalization of the seizure through the brain (Swartz & Larson 1986). We have reported that several of the noted signs of high therapeutic value can fail to occur when other signs of high therapeutic value do occur, e.g., motor seizure can fail to occur while strong postictal suppression occurs, and vice-versa (Swartz 1996).

Such aggregate measures include an Aggregate Flaw measure, and an Aggregate Concordance measure. The Aggregate Flaw measure scores the number of measures that failed to show seizure strength among all measures used. For example, use of the following measures would provide seven values to compare with corresponding thresholds for good effect: peak 10-second EEG area rate, peak 10-second EEG concordance, time to onset of high-amplitude low-frequency waves, ratio of minimum postictal EEG area rate to pre-treatment EEG area rate, peak heart rate, number of muscle EMG spikes, and duration of motor seizure. The number of such values that did not cross the thresholds for good effect forms the Aggregate Flaw measure. An Aggregate Flaw result of 0 is a sign of a strong seizure, a result of 7 is a sign of little therapeutic value, and intermediate values are signs of intermediate value. Preferably the thresholds are based on group norms obtained from similar patients, i.e., age and sex. The thresholds are stored in computer memory in the ECT device.

An Aggregate Concordance measure describes the amount of spread among measures of seizure duration derived from the EEG, the ECG, and the EMG, to reflect the degree of simultaneously and spread of the seizure through the brain. The EEG-derived seizure duration measurement would be as described in U.S. Pat. No. 5,269,302, incorporated by reference herein. The ECT-derived seizure duration is the time from the end of the electrical stimulus to the end of persistence of the heart rate within a particular percentage of the peak heart rate, for example, within 10% of the peak heart rate. The EMG-derived seizure duration is the time from the end of the electrical stimulus to the last motor contraction. The Aggregate Concordance measure would be calculated by taking the absolute values of the differences between the 3 durations and their mean, averaging them, expressing this average as a percentage of said mean, and subtracting said average from 100%. This expression will not become negative.

Traditionally, the physician has had only clinical signs and symptoms to guide him in the determination of the cumulative clinical efficacy of the course of CT treatments he is administering—no objective laboratory tests exist to aid him in this process. The clinical assessment of psychiatric patients is often unreliable because patients may be mute, uncooperative, and may minimize or exaggerate their symptoms, depending on their mental state at the time of interview.

The EEG Index, as well as an EEG Delta Index, and EEG Alpha Index provides an objective measure of brain function that the psychiatrist can consider, together with the clinical data in making a decision whether to administer—or withhold—further CT treatment The EEG Index is analogous to blood level determinations of the therapeutic levels of the various psychopharmacologic medications used to treat psychiatric patients. If a patient is not responding as expected to a particular drug, and the blood level of that drug is observed not to have reached the therapeutic range, the treating physician may decide to increase the dosage or frequency of administration of the medication. Similarly, if a patient receiving ECT is not responding as expected, and the EEG Index reflects an insufficient accumulation of, e.g., EEG delta activity that is below the therapeutic range, the treating physician may decide to increase the dosage or frequency of the ECTs.

The report by Fink and Kohn (1957) indicates that the cumulative EEG slowing (specifically in the delta range), induced by a series of ECT treatment, was a significant predictor of clinical response to the treatment course. Recently, their work was confirmed by Sackeim et al (1996) in a sample of 62 inpatients with unilateral or bilateral ECT given at high or low dosages. In this study, effective forms of ECT (i.e., both forms of bilateral ECT, and high dose unilateral ECT) increased interictal delta power in prefrontal brain regions, an increase that correlated significantly with the degree of rated clinical improvement.

The "EEG Index" is the energy (power) over the entire bandwidth. The "Delta Index" etc. is the energy (power) over the Delta (or corresponding) bandwidth. During the range 0 to 30 min. (preferably 2 to 5 min.) immediately prior to administering the first seizure of the treatment course (whether electrically or magnetically induced) a sample of baseline EEG is obtained, digitized, subjected to Fast Fourier Transform (FFT) analysis across the range of 0 to 60 Hz frequency bandwidth (preferably 2 to 8 Hz). The energy or power in each EEG bandwidth (delta, theta, alpha, beta) is stored or printed out for future reference.

This procedure is repeated at each subsequent treatment. This allows the treating physician to assess the absolute and rate of increase in the EEG Index induced by each ECT treatment, and to adjust the dosage or frequency of administration accordingly.

REFERENCES

Abrams, R., Swartz C. M., Vedak C. Antidepressant effects of high-dose right unilateral ECT. Arch Gen Psychiatry 1991; 48:746–748.

Christensen P., Kragh Sorensen P., Sorensen C., Thomsen H. Y., Iversen A. D., Christensen K. S., Huttel M., Tonnesen E. EEG-monitored ECT: A comparison of seizure duration under anesthesia with etomidate and thiopentone. Convulsive Ther 1986; 2:145–150.

Fink M., Kahn R. L. (1957): Relation of EEG Delta activity to behavioral response in electroshock: Quantitative serial studies. Arch Neurol Psychiatry 78:516–525.

Krystal A. D., Weiner R. D., McCall W. V., et al. The effects of ECT stimulus dose and electrode placement on the ictal electroencephalogram: an intra-individual cross-over study. Biol Psychiatry 1993; 34:759–767.

Krystal A. D., Weiner R. D., Coffey C. E. The ictal EEG as a marker of adequate stimulus intensity with unilateral ECT. J Neuropsychiatry Clin Neurosci 1995; 7:295–303.

Krystal A. D., Weiner R. D., Gassert D., McCall W. V., Coffey C. E., Silbert T., Holsinger T. The relative ability of three ictal EEG frequency bands to differentiate ECT seizures on the basis of electrode placement, stimulus intensity, and therapeutic response. Convulsive Ther 1996; 12:13–24.

Lane R. D., Zeitlin S. B., Abrams R., Swartz C. M. Differential effects of right-unilateral and bilateral ECT on heart rate. Am J Psychiatry 1989; 146:1041–1043.

Nobler M. S., Sackeim H. A., Solomou M., Luber B., Devanand D. P., Prudic J. EEG manifestations during ECT; effects of electrode placement and stimulus intensity. Biol Psychiatry 1993: 34:321–330.

Sackheim, H. A., Luber B. L., Katzman G. P., Moeller J. R., Prudic J., Devanand D. P., Nobler M. S. (1996): The effects of electroconvulsive therapy on quantitative EEG: Relationship to clinical outcome. Arch. Gen. Psychiatry 53:814–824

Swartz C. M., Generalization, duration, and low-frequency EEG persistence of bilateral ECT seizure. Biol Psychiatry 1995; 38:837–842.

Swartz C. M., Larson G. Generalization of the effects of unilateral and bilateral ECT. Am J Psychiatry 1986; 143:1040–1041.

Swartz C. M., Larson G. ECT Stimulus Duration and its efficacy. Ann Clin Psychiatry 1989; 1:147–152.

Swartz, C. M. Disconnection of EEG, Motoric, and Cardiac Evidence of ECT Seizure, Convulsive Ther 1996; 12(i):25–30.

Swartz, C. M., Manly, D. report in progress.

Webb, M. C., Coffey C. E., Saunders W. R., Cress M. M., Weiner R. D., Sibert T. R. Cardiovascular response to unilateral electroconvulsive therapy. Biol Psychiatry 28:758–766, 1990.

We claim:

1. A method of convulsive therapy (CT), which comprises electroconvulsive therapy (ECT) and magnetoconvulsive therapy (MCT) to measure physiological aspects of the CT seizure of a patient and to describe the therapeutic value of the therapy, including the steps of:

(a) employing a CT device having a computer system therein, removably securing an output means of the CT device on, or proximate to, the head of the patient and applying power to the output means to provide a stimulus in a convulsive therapy session with the expectation of inducing seizure;

(b) detecting the brain wave activity of the patient by amplification of the electrical signals from the brain using an electroencephalographic (EEG) device and electrodes removably attached to the patient's head;

(c) repeatedly converting the amplified EEG signals into a set of digitalized samples of the brain wave amplitude over a selected time interval of 0.1 to 3 seconds and numerically integrating the samples to constitute a sequence of post-stimulus EEG area rates;

(d) displaying the sequence of said EEG area rates; and (e) displaying the sequence of EEG area rates in summary form at the end of the CT treatment.

2. A method of convulsive therapy (CT), which comprises electroconvulsive therapy (ECT) and magnetoconvulsive therapy (MCT), to measure physiological aspects of the CT seizure of a patient and to describe the therapeutic value of the therapy, including the steps of:

(a) employing a CT device having a computer system therein, removably securing an output means of the CT device on, or proximate to, the head of the patient and applying power to the output means to provide a stimulus in a convulsive therapy session with the expectation of inducing seizure;

(b) detecting the brain wave activity of the patient by amplification of the electrical signals from the brain using an electroencephalographic (EEG) device and electrodes removably attached to the patient's head;

(c) repeatedly converting the amplified EEG signals into a set of digitalized samples of the brain wave amplitude over a selected time interval of 0.1 to 3 second and numerically integrating the samples to constitute a sequence of post-stimulus EEG area rates;

(d) displaying the sequence of said EEG area rates;

(e) measuring the brain wave activity of the patient prior to the therapy by amplification of the patient's electrical signals from the brain using the EEG device and electrodes removably attached to the patient's head;

(f) repeatedly converting the amplified EEG signals into a set of digitalized samples of the brain wave amplitude over a selected time interval of 0.1 to 3 seconds and numerically integrating the samples to constitute a sequence of pre-therapy EEG area rates;

(g) in the computer system, comparing the pre-stimulus EEG area rates and the post-stimulus EEG area rates; and (h) displaying the results of the comparisons.

3. A method as in claim 2 wherein the selected time interval is about 1 second.

4. A method as in claim 2 including the steps of obtaining and displaying a sequence of post-stimulus EEG area rates covering the time that any post-stimulus EEG area rate exceeds a pre-stimulus EEG area rate, thereby obtaining a measurement of the endpoint and duration of the seizure and the peak and total EEG area rates during the seizure.

5. A method as in claim 2 and measuring and displaying time measured from the termination of the stimulus to onset of high-amplitude low-frequency brain waves of the patient.

6. A method as in claim 5 wherein displaying time measured comprises displaying the time to reach within a selected percentage of peak EEG voltage or peak EEG area rate.

7. A method as in claim 2 and measuring and displaying a ratio of the minimum post-stimulus EEG area rate to the pre-stimulus EEG area rate, thereby expressing a measurement of postictal suppression.

8. A method as in claim 2 and measuring and displaying a ratio of a peak post-stimulus EEG area rate to a pre-stimulus EEG area rate.

9. A method as in claim 2 and measuring a minima postictal EEG area rate and in the computer system comparing the baseline pre-stimulus EEG area rate to the postictal minima EEG area rate to provide an indication of the suppression of the baseline pre-stimulus EEG area rate due to the seizure; and displaying the results of the comparison.

10. A method of convulsive therapy (CT), which comprises electroconvulsive therapy (ECT) and magnetoconvulsive therapy (MCT), to measure physiological aspects of the CT seizure of a patient and to describe the therapeutic value of the therapy, including the steps of:

(a) employing a CT device having a computer system therein, removably securing an output means of the CT device on, or proximate to, the head of the patient and applying power to the output means to provide a stimulus in a convulsive therapy session with the expectation of inducing seizure;

(b) detecting the brain wave activity of the patient by amplification of the electrical signals from the brain using an electroencephalographic (EEG) device and electrodes removably attached to the patient's head;

(c) repeatedly converting the amplified EEG signals into a set of digitalized samples of the brain wave amplitude over a selected time interval of 0.1 to 3 seconds and numerically integrating the samples to constitute a sequence of post-stimulus EEG area rates;

(d) displaying the sequence of said EEG area rates; and (e) measuring and displaying a ratio of a minimum post-stimulus EEG area rate to a peak post-stimulus EEG area rate.

11. A method of convulsive therapy (CT), which comprises electroconvulsive therapy (ECT) and magnetoconvulsive therapy (MCT), to measure physiological aspects of the CT seizure of a patient and to describe the therapeutic value of the therapy, including the steps of:

(a) employing a CT device having a computer system therein, removably securing an output means of the CT device on, or proximate to, the head of the patient and applying power to the output means to provide a stimulus in a convulsive therapy session with the expectation of inducing seizure;

(b) detecting the brain wave activity of the patient by amplification of the electrical signals form the brain using an electroencephalographic (EEG) device and electrodes removably attached to the patient's head;

(c) repeatedly converting the amplified EEG signals into a set of digitalized samples of the brain wave amplitude over a selected time interval of 0.1 to 3 seconds and numerically integrating the samples to constitute a sequence of post-stimulus EEG area rates;

(d) displaying the sequence of said EEG area rates; and (e) measuring a plurality of post-stimulus EEG area rates and calculating, in the computer system, the maxima and minima of said plurality and their times of occurrence.

12. A method as in claim 11 and displaying the times of occurrence of the maxima and minima post-stimulus EEG area rates.

13. A method as in claim 11 and calculating, in the computer system, a Suppression of Seizure Activity index based upon a comparison of the minima EEG post-stimulus EEG area rate to the maxima post-stimulus EEG area rate.

14. A method of convulsive therapy comprising electroconvulsive therapy (ECT) and magnetoconvulsive therapy (MCT), to measure physiological aspects of the CT seizure of a patient that describe the therapeutic value of the therapy, including the steps of:

(a) amplifying electrical signals from the patient's brain using an electroencephalographic (EEG) device having an electrode removably attached to the head of the patient, converting the EEG signals into a first set of EEG data, setting a baseline EEG reference based on the first set of EEG data, and storing the baseline EEG reference in a computer system having memory;

(b) employing a CT device having the computer system and removably securing an output means of the CT device on, or proximate, the head of the patient and applying power thereto to provide a stimulus in a convulsive therapy session with the expectation of inducing seizure;

(c) detecting the brain wave activity of the patient by amplification of the electrical signals from the brain using the EEG device and removable electrodes, converting the amplified EEG signals into a second set of EEG data, and measuring the time that the second set of EEG data exceeds the baseline EEG reference;

(d) displaying said time; and (e) converting the brainwaves into the first set and the second set of EEG data by digitizing samples of brain wave amplitudes over selected time intervals of 0.1 to 3 seconds and numerically integrating the samples to generate a pre-therapy EEG area rate as the baseline EEG reference and a sequence of post-stimulus EEG area rates as the second set of EEG data.

15. A method of convulsive therapy (CT), which comprises electroconvulsive therapy (ECT) and magnetoconvulsive therapy (MCT), to measure physiological aspects of the CT seizure of a patient that describe the therapeutic value of the therapy, including the steps of:

(a) detecting brain wave activity of the patient prior to the CT by amplifying electrical signals from the patient's brain using an electroencephalographic (EEG) device having an electrode removably attached to the head of the patient, converting the EEG signals into baseline EEG data, and storing the baseline EEG data in a computer system having memory;

(b) employing a CT device having the computer system therein and removably securing an output means of electrodes of the CT device on, or proximate to, the head of the patient and applying power thereto in a convulsive therapy session with the expectation of inducing seizure;

(c) in the range of less than 30 seconds immediately following termination of the application of power to induce the seizure by the CT device, commencing detecting the brain wave activity of the patient by amplification of the electrical signals from the brain using the EEG device and removable electrode and converting the amplified EEG signals into a second set of EEG data that describe the minimum postictal EEG amplitude; and (d) calculating, in the computer system, and displaying the ratio of the minimum postictal EEG amplitude to the baseline EEG data.

16. A method as in claim 15 and converting the brain waves into the baseline EEG data and minimum postictal EEG by digitalizing samples of brain wave amplitudes over selected time intervals of 0.1 to 3 seconds and numerically integrating the samples to generate a pre-stimulus EEG area rate as the baseline data and a minimum postictal EEG area rate as the minimum postictal EEG.

17. A method of convulsive therapy (CT), which comprises electroconvulsive therapy (ECT) and magnetoconvulsive therapy (MCT), to measure physiological aspects of the CT seizure of a patient and to describe the therapeutic value of the therapy, including the steps of:

(a) employing a CT device having a computer system therein, removably securing an output means of the CT device on, or proximate to, the head of the patient and applying power to the output means to provide a stimulus in a convulsive therapy session with the expectation of inducing seizure;

(b) in the range of less than 30 seconds immediately following termination of the stimulus, commencing detecting brain wave activity of the patient by amplification of electrical signals from two opposite sides of the brain using an electroencephalographic (EEG) device and electrodes removably attached opposite each other in pairs on opposite sides of the patient's head;

(c) converting the amplified EEG signals into a set of digitalized samples of the brain wave amplitude over selected time intervals;

(d) in the computer system, analyzing the voltage differences between the digitalized samples from the electrodes within each pair and generating a seizure coherence measurement based upon the analysis; and (e) displaying the seizure coherence measurement.

18. A method as in claim 17 wherein in (d) the analysis includes subtracting the voltage differences of each pair from a mean voltage of a plurality of pairs.

19. A method as in claim 17 wherein in (d) the analysis includes calculating at a sequence taken over time and in (e) the absolute values are displayed.

20. A method as in claim 17 wherein in (d) the analysis includes obtaining a sum of the voltage differences which is subtracted from a mean voltage.

21. A method as in claim 17 wherein in (d) analyzing the voltage differences comprises subtracting voltages over a selected time period from 0.5 to 3 seconds in length.

22. A method as in claim 21 wherein in (d) a regression coefficient or correlation coefficient is calculated based on the time period and in (e) at least one of the coefficients is displayed.

23. A method as in claim 17 wherein the seizure coherence measurement is derived from one, or more, of the following:

(i) momentary peak coherence during the seizure;

(ii) a selected time period of maximum peak coherence during the seizure;

(iii) momentary minimum coherence after the seizure;

(iv) a selected time period of minimum coherence after the seizures;

(v) coherence measurements pre-treatment as a baseline; and (vi) coherence measurements in one or more of the selected bands of frequencies from 2.5 to 30 Hz.

24. A method of convulsive therapy (CT), comprising electroconvulsive therapy (ECT) and magnetoconvulsive therapy (MCV), to measure physiological aspects of the CT seizure of a patient that describe the therapeutic value of the therapy, including the steps, in order, of:

(a) detecting heartbeat rate of the patient by amplifying the electrical signals form the patient's heart using an electrocardiograph (ECG) device having electrodes removably attached to the skin of the patient, converting the ECG heartbeat signals into a first set of digital ECG heart rate data representing a pre-treatment heart rate; storing in a computer system having memory the first set of ECG data; and (b) employing a CT device having the computer system therein and removably positioning an output means of the CT device on, or proximate to, the head of the patient and applying power to the output means to provide stimulus in a convulsive therapy session with the expectation of inducing seizure;

(c) monitoring the post-stimulus heart rate of patient by amplification of the electrical signals from the heart using the ECG device and removable electrodes and converting the amplified ECG signals into a second set of heart rate data in order to compare, in the computer system, the first and second sets of heart rate data and to determine the duration of heart rate elevation starting at the end of the stimulus and including a peak heart rate and terminating at the post-peak time at which the heart rate exceeds both: (i) the pre-treatment heart rate; and (ii) remains within a selected amount which is about 10% of the peak heart rate or a selected percentage of the peak heart rate; and (d) displaying said duration of heart rate elevation.

25. A method of convulsive therapy (CT), comprising electroconvulsive therapy (ECT) and magnetoconvulsive therapy (MCV), to measure physiological aspects of the CT seizure of a patient that describe the therapeutic value of the therapy, including the steps, in order, of:

(a) detecting heartbeat rate of the patient by amplifying the electrical signals form the patient's heart using an electrocardiograph (ECG) device having electrodes removably attached to the skin of the patient, converting the ECT heartbeat rate signals into a first set of digital ECG heart rate data representing a pre-treatment heart rate; storing in a computer system having memory the first set of ECG data;

(b) employing a CT device having the computer system therein and removably positioning an output means of the CT device on, or proximate to, the head of the patient and applying power to the output means to provide stimulus in a convulsive therapy session with the expectation of inducing seizure;

(c) monitoring the post-stimulus heart rate of the patient by amplification of the electrical signals from the heart using the ECG device and removable electrodes and converting the amplified ECG signals into a second set of heart rate data in order to compare, in the computer system, the first and second sets of heart rate data and to determine the duration of heart rate elevation starting at the end of the stimulus and including a peak heart rate and terminating at the post-peak time at which the heart rate exceeds both: (i) the pre-treatment heart rate; and (ii) remains within a selected amount of the peak heart rate or a selected percentage of the peak heart rate;

in which the peak heart rate is a momentary peak heart rate; and (d) displaying said duration of heart rate elevation.

26. A method as in claim 25 wherein the heart rate elevation is defined by determining when the post-stimulus heart rate exceeds the pre-treatment heart rate and remains within a selected amount of the peak heart beat rate by an amount that is about 10 beats per minute.

27. A method as in claim 26 in which the peak heart rate is the peak as sustained over a selected period of time or a selected number of heart beats.

28. A method as in claim 25 and measuring and displaying heart beat rate during the course of the CT treatment.

29. A method of convulsive therapy (CT), which comprises electroconvulsive therapy (ECT) or magnetoconvulsive therapy (MCT), to measure physiological aspects of the CT seizure of a patient that describe the therapeutic value of the therapy, including the steps of:

(a) employing a CT device having a computer system therein, removably securing an output means of the CT device on, or proximate to, the head of the patient and applying power thereto to provide a stimulus in a convulsive therapy session with the expectation of inducing seizure;

(b) in the range of less than 30 seconds immediately following termination of the stimulus, commencing detecting the muscle activity of a muscle of the patient by amplification of the electrical signals from a muscle of the patient using an EMG device and removable electrodes and converting the amplified EMG signals into EMG data;

(c) based on the EMG data, counting the number of electrical spikes generated by the muscle; and (d) displaying the number of EMG electrical spikes.

30. A method as in claim 29 and measuring any pauses in the spikes which exceed a selected time.

31. A method as in claim 29 and measuring and displaying the total duration of time that the electrical spikes are produced commencing at the end of the stimulus.

32. A method of measuring aspects of convulsive therapy (CT) induced seizure that describes the therapeutic value of the therapy, said method including the steps of:

(a) determining a value of at least five of the following measures immediately following the therapy;
  i. peak 10-second EEG area rate;
  ii. peak 10-second EEG concordance;
  iii. time to onset of high-amplitude low-frequency waves;
  iv. ratio of minimum postictal EEG area rate to pre-treatment EEG area rate;
  v. peak heart rate;
  vi. number of muscle EMG spikes; and
  vii. duration of motor seizure;

(b) in a computer system, comparing the value of each of the measures to a predetermined threshold value for the same measure, the threshold values being based on group norms;

(c) in the computer system, determining if each of the measured values is below the predetermined threshold value for that measure;

(d) in the computer system, determining an Aggregate Flaw Measure (AFM) by calculation of those measures having values below their predetermined threshold values; and (e) displaying the Aggregate Flaw Measure.

33. A method as in claim 32 wherein the predetermined value for each of the measures in (a) is based on standard values obtained from a group of patients of similar age and sex.

34. A method of measuring physiological aspects of a convulsive therapy (CV) induced seizure that describes the degree of simultaneity and spread of the seizure through the brain of a patient, said method including the steps of:

(a) measuring duration of the seizure using an electroencephalograph (EEG) device;

(b) measuring duration of the seizure using an electrocardiograph (ECG) device by measuring and calculating, using a computer system, the time from the end of the electrical stimulus to the end of persistence of the heart rate within a predetermined percentage of the heart rate peak;

(c) measuring duration of the seizure using an electromyograph (EMG) device from the end of the electrical stimulus to the last motor contraction;

(d) in the computer system, determining a mean of the durations of the seizure obtained from EEG, ECG, and EMG;

(e) in the computer system, determining differences between the mean and each of the durations of the seizure obtained by the EEG, ECT, and EMG;

(f) in the computer system, generating an Aggregate Concordance Measure (ACM) by calculations based on the determinations of (e); and (g) displaying the Aggregate Concordance Measure.

35. A method as in claim 34 wherein the calculations of (f) are based upon:

determining an absolute value of the differences;

determining an average of the absolute values determined in (e); and determining a product by multiplying said average by 100% and then determining a result by dividing said product by said mean.

36. A method of magnetoconvulsive therapy (MCT) to measure physiological aspects of the MCT seizure that describe the therapeutic value of the therapy, including the steps of:

(a) amplifying the electrical signals from the brain using an electroencephalographic (EEG) device having an electrode removably attached to the head of the patient to detect EEG signals, converting the EEG signals into a first set of EEG data, setting a baseline EEG reference based on the first set of EEG data, and storing in computer system memory the baseline EEG reference;

(b) employing an MCT device, removably securing an output means of the MCT device on, or proximate, the head of the patient and applying power thereto in a convulsive therapy session with the expectation of inducing seizure;

(c) in the range of less than 30 seconds immediately following termination of the application of power to induce the seizure by the MCT device commencing detecting the brain wave activity of the patient by amplification of the electrical signals from the brain using an EEG device and removable electrodes, converting the amplified EEG signals into a second digital set of EEG data, using a computer system to calculate the time that the second set of EEG data exceeds the baseline EEG reference; and (d) displaying said time.

37. A method of magnetoconvulsive therapy (MCT) to measure physiological aspects of the MCT seizure of a patient and to describe the therapeutic value of the therapy, including the steps of:

(a) employing an MCT device, removably securing an output coil of the MCT device, on, or proximate, the head of the patient and applying power to the output coil in a convulsive therapy session to induce seizure;

(b) in the range of less than 30 seconds immediately following termination of the application of power to induce the seizure by the MCT device, commencing detecting the brain wave activity of the patient by amplification of the electrical signals from the brain using an electroencephalographic (EEG) device and electrodes removably attached to the patient's head;

(c) converting the amplified EEG signals into a set of digitalized samples of the brain wave amplitude and integrating the samples to constitute a post-stimulus EEG area representing power; and (d) displaying said post-stimulus EEG power.

38. A method of convulsive therapy (CT), which comprises electroconvulsive therapy (ECT) and magnetoconvulsive therapy (MCT), to measure physiological aspects of the CT seizure of a patient and to describe the therapeutic value of the therapy, including the steps of:

(a) in the range of less than 30 minutes immediately preceding one CT, detecting the brain wave activity of the patient by placing EEG electrodes on the scalp of the patient and amplification and digitizing of the electrical signals from the patient's brain using an electroencephalographic (EEG) device to obtain a baseline EEG Index, which is a measure of energy or power in one or more bandwidths;

(b) recording the baseline EEG Index;

(c) prior to a next CT treatment, repeating step (a) to obtain a subsequent EEG Index;

(d) comparing the baseline EEG index to the subsequent treatment EEG Index and adjusting the dosage or frequency of subsequent CV treatment based on the comparison.

39. A method as in claim 38 wherein the range is (a) is from 2 to 5 minutes.

40. A method as in claim 38 including performing a Fast Fourier Transform (FFT) on the brain activity in (a) and wherein the bandwidth on which the FFT is performed is in the range of 0–60 Hz.

41. A method as in claim 40 wherein the said bandwidth is in the range of 2–8 Hz.

42. A method as in claim 38 including performing a Fast Fourier Transform (FFT) on the brain wave activity in (a).

43. An apparatus in convulsive therapy (CT), which comprises electroconvulsive therapy (ECT) and magnetoconvulsive therapy (MCT), to measure physiological aspects of the CT seizure of a patient and to display measurements indicating the therapeutic value of the therapy, the apparatus being a unitary instrument having an internal computer system, the apparatus including:

(a) EEG means to detect the brain wave activity of the patient prior to the CT by amplifying the electrical signals from the patient's brain; the EEG means including an electroencephalographic (EEG) device having an electrode removably attached to the head of the patient to detect and amplify EEG signals, analog/digital conversion means to convert the amplified EEG signals into a first set of EEG samples, baseline means in the computer system to derive an EEG baseline area rate based on numerically integrating the samples taken over a period of 0.1 to 3 seconds and averaged, and memory means in the computer system to record EEG baseline area rate;

(b) a CT device, including an output means adapted to be secured on, or proximate to, the head of the patient and means to apply power thereto in a convulsive therapy session with the expectation of inducing seizure;

(c) means to detect and record in the memory means the postictal brain wave activity of the patient, commencing in the range of less than 30 seconds immediately following termination of the application of power to induce the seizure by the CT device, by amplification of the electrical signals from the brain using the EEG device and removable electrode;

(d) means to convert and numerically integrate the amplified postictal EEG signals into a second set of EEG samples that describe the postictal EEG area rate over a selected time interval of from 0.1 to 3 seconds;

(e) means in the computer system to compare, and generate a ratio of, the postictal EEG area rate and the baseline area rate; and (f) means to display the ratio of the postictal EEG area rate to the baseline area rate.

44. An apparatus as in claim 43 and means to measure and display the time to onset of the patient's postictal brain waves which are of high-amplitude within 20% of peak EEG voltage or peak area rate) and low-frequency (below 12 Hz) brain waves.

45. An apparatus as in claim 43 and means to calculate and display a ratio of a minimum postictal EEG area rate to pre-treatment EEG area rate.

46. Apparatus as in claim 43 and means to calculate and display a ratio of a minimum postictal EEG area rate to the peak post-stimulus EEG area rate.

47. Apparatus in convulsive therapy (CT), which comprises electroconvulsive therapy (ECT) and magnetoconvulsive therapy (MCT), to measure physiological aspects of the CT seizure and to display measurements indicating the therapeutic value to a patient of the therapy, the apparatus being a unitary instrument having an internal computer system, the apparatus including:

(a) EEG means to detect the brain wave activity of the patient prior to the CT by amplifying the electrical signals from the patient's brain; the EEG means including an electroencephalographic (EEG) device having an electrode removably attached to the head of the patient to detect and amplify EEG signals, analog/digital conversion means to convert the amplified EEG signals into a first set of EEG samples, baseline means in the computer system to derive an EEG baseline area rate based on numerically integrating the first set of EEG samples taken over a period of 0.1 to 3 seconds, and memory means in the computer to record the EEG baseline area rate;

(b) a CT device, including an output means adapted to be secured on, or proximate to, the head of the patient and means to apply power thereto in a convulsive therapy session with the expectation of inducing seizure;

(c) means to detect and record in the computer system memory the postictal brain wave activity of the patient, commencing in the range of less than 30 seconds immediately following termination of the application of power to induce the seizure by the CT device, by amplification of the electrical signals from the brain using the EEG device and removable electrode;

(d) means to convert the amplified postictal EEG signals into a second set of EEG samples that describe the postictal peak EEG area rate over a selected time interval of from 0.1 to 3 seconds;

(e) computer means to compare and generate the time that the EEG area rate exceeds the baseline area rate; and (f) means to display the time that the peak EEG area rate exceeds the baseline area rate.

48. Apparatus as in claim 47 and means to measure and display the time to onset of the patient's postictal high-amplitude (within 20% of peak EEG voltage or area rate) and low-frequency (2–12.5 Hz) brain waves.

49. Apparatus as in claim 47 and means to calculate and display a ratio of a minimum postictal EEG area rate to baseline EEG area rate.

50. Apparatus as in claim 47 and means to calculate and display a ratio of a minimum postictal EEG area rate to the postictal peak EEG area rate.

51. Apparatus in convulsive therapy (CT), which comprises electroconvulsive therapy (ECT) and magnetoconvulsive therapy (MCT), to measure physiological aspects of the CT seizure and to display measurements indicating the therapeutic value to a patient of the therapy, the apparatus being a unitary instrument having an internal computer system, the apparatus including:

(a) EEG means to detect the brain wave activity of the patient prior to the CT by amplifying the electrical signals from the patient's brain; the EEG means including an electroencephalographic (EEG) device having an electrode removably attached to the head of the patient to detect and amplify EEG signals, analog/digital conversion means to convert the amplified EEG signals into a first set of EEG samples, baseline means in the computer system to derive an EEG baseline area rate based on numerically integrating the samples taken over a period of 0.1 to 3 seconds, and memory means in the computer system to record the EEG baseline area rate;

(b) a CT device, including an output means adapted to be secured on, or proximate, the head of the patient and means to apply power thereto in a convulsive therapy session with the expectation of inducing seizure;

(c) means to detect and record, in the memory of the computer system, the postictal brain wave activity of the patient, commencing in the range of less than 30 seconds immediately following termination of the application of electricity to induce the seizure, by amplification of the electrical signals from the brain using the EEG device and removable electrode;

(d) means to convert the amplified EEG signals into a second set of EEG samples, over a selected time interval of from 0.1 to 3 seconds that describe the minimum postictal EEG area rate;

(e) computer means to compare, and generate a ratio, of the minimum postictal EEG area rate to the baseline area rate; and (f) means to display said ratio.

52. Apparatus as in claim 51 and means to measure and display the time to onset of the patient's post-stimulus high-amplitude low-frequency waves.

53. Apparatus as in claim 51 and means to display the ratio of the minimum postictal EEG area rate to postictal peak EEG area rate.

* * * * *